United States Patent [19]

Morris et al.

[11] Patent Number: 5,372,784

[45] Date of Patent: Dec. 13, 1994

[54] MEASUREMENT OF BACTERIAL CO₂ PRODUCTION IN AN ISOLATED FLUOROPHORE BY MONITORING AN ABSORBANCE REGULATED CHANGE OF FLUORESCENCE

[75] Inventors: Roger J. Morris, Sacramento; Shoshana Bascomb, Davis; Carolyn S. Olson, Sacramento; Jamie Bobolis, Sacramento; David Sherman, Sacramento, all of Calif.

[73] Assignee: Baxter Diagnostics Inc., Deerfield, Ill.

[21] Appl. No.: 212,674

[22] Filed: Mar. 11, 1994

Related U.S. Application Data

[63] Continuation of Ser. No. 638,481, Jan. 4, 1991, abandoned, which is a continuation-in-part of Ser. No. 609,278, Nov. 5, 1990, Pat. No. 5,173,434, and a continuation-in-part of Ser. No. 238,710, Aug. 31, 1988, abandoned.

[51] Int. Cl.⁵ .............................................. G01N 21/76
[52] U.S. Cl. ...................... 422/82.08; 422/52; 422/55; 422/56; 422/82.05; 422/82.07; 435/34; 435/39; 435/291; 435/808; 436/167; 436/169; 436/170; 436/172
[58] Field of Search ................... 422/55, 56, 52, 82.05, 422/82.07, 82.08; 435/34, 39, 808, 291; 436/167, 169, 170, 172, 800

[56] References Cited

U.S. PATENT DOCUMENTS

| | | |
|---|---|---|
| Re. 31,879 | 5/1985 | Lubbers et al. . |
| 3,676,679 | 7/1972 | Waters . |
| 4,073,691 | 2/1978 | Ahnell et al. . |
| 4,152,213 | 5/1979 | Ahnell . |
| 4,182,656 | 1/1980 | Ahnell et al. . |
| 4,231,754 | 11/1980 | Vogelhut ............................ 436/172 |
| 4,495,293 | 1/1985 | Shaffer . |
| 4,563,907 | 3/1987 | Freundlich . |
| 4,672,039 | 6/1987 | Lundblom . |
| 4,698,308 | 10/1987 | Ikeda . |
| 4,772,558 | 9/1988 | Hammann . |
| 4,780,191 | 10/1988 | Romette et al. . |
| 4,784,947 | 11/1988 | Noeller . |
| 4,798,788 | 1/1989 | Sands . |
| 4,803,049 | 2/1989 | Hirschfeld et al. .......... 422/82.07 X |
| 4,851,195 | 7/1989 | Matthews et al. ............... 422/82.07 |
| 4,945,060 | 7/1990 | Turner et al. . |
| 5,093,266 | 3/1992 | Leader et al. ................. 422/82.08 X |
| 5,114,676 | 5/1992 | Leiner et al. ................. 422/82.07 X |
| 5,143,853 | 9/1992 | Walt ................................ 436/172 X |
| 5,164,301 | 11/1992 | Thompson et al. ............ 436/172 X |
| 5,232,858 | 8/1993 | Wolfbeis et al. ................. 436/172 X |

FOREIGN PATENT DOCUMENTS

| | | |
|---|---|---|
| 0091837 | 4/1984 | European Pat. Off. . |
| 0104463 | 4/1984 | European Pat. Off. . |
| 0124193 | 11/1984 | European Pat. Off. . |
| 0171158 | 2/1986 | European Pat. Off. . |
| 1601689 | 11/1981 | United Kingdom . |

OTHER PUBLICATIONS

Ando et al., Pyruvate as a Fluorescence Quencher: A New Spectroscopic Assay for Pyruvate Reactions, Anal. Bio. 129, 170–175 (1983).

Shoshana Bascomb, Enzyme Tests in Bacterial Identification, Method in Microbiology, 19: 105 (1987).

(List continued on next page.)

Primary Examiner—James C. Housel
Assistant Examiner—Maureen M. Wallenhorst
Attorney, Agent, or Firm—Mark J. Buonaiuto; Cynthia G. Tymeson; Paul C. Flattery

[57] ABSTRACT

A multi-layer blood culture sensor includes two matrices. The first matrix is a polymer that is permeable to carbon dioxide and water, but impermeable to protons. A pH sensitive absorbance based dye is encapsulated or isolated in the polymer. The second matrix is a polymer with a pH insensitive fluorescent dye encapsulated or isolated in the polymer. The matrices are spectrally coupled and are useful for the determination of microorganisms in a blood culture bottle.

4 Claims, 5 Drawing Sheets

OTHER PUBLICATIONS

Blumberg et al., *Hemoglobin Determined in 15 μL of Whole Blood by "Front-Face" Fluorometry*, Clin. Chem. 26/3, 409–413 (1980).

Carmel et al., An Intramolecularly Quenched Fluorescent Tripeptide as a Flurogenic Substrate of Angiotensin-I-Converting Enzyme and of Bacterial Dipeptidyl Carboxypeptidase, Eur. J. Biochem., 87 265–273 (1978).

Carmel et al., Intramolecularly-Quenched Fluorescent Tripeptide as a Fluorogenic Substrates of Leucine Aminopeptidase and Inhibitors of Clostridial Aminopeptidase, Eur. J. Biochem., 73, 617–625 (1977).

Fleminger et al., Fluorogenic Substrates for Bacterial Aminopeptidase P and Its Analogs Detected in Human Serum and Calf Lung, Eur. J. Biochem., 125, 609–615 (1982).

Florentin et al., A Highly Sensitive Fluorometric Assay for "Enkephalinase," a Neutral Metalloendopeptidase That Releases Tyrosine-Glycine-Glycine from Enkephalins, Anal. Biochem. 141, 62–69 (1984).

Rhines et al., Simplex Optimization of a Fiber-Optic Ammonia Sensor Based on Multiple Indicators, Anal. Chem., 60, 76–81 (1988).

Wolfbeis et al., Fibre-Optic Fluorescing Sensor for Ammonia, Anal. Chimica Acta, 185, 321–327 (1986).

Yaron et al., Intramolecularly Quenched Fluorogenic Substrates for Hydrolytic Enzymes, Anal. Biochem., 95, 228–235 (1979).

MEASUREMENT OF BACTERIAL CO$_2$ PRODUCTION IN AN ISOLATED FLUOROPHORE BY MONITORING AN ABSORBANCE REGULATED CHANGE OF FLUORESCENCE

This application is a continuation of application Ser. No. 07/638,481, filed on Jan. 4, 1991, now abandoned, which is a continuation-in-part of application Ser. No. 07/609,278, filed on Nov. 5, 1990 and now U.S. Pat. No. 5,173,434 issued on Dec. 22, 1992, as well as a continuation-in-part of application Ser. No. 07/238,710, filed on Aug. 31, 1988 and now abandoned.

FIELD OF THE INVENTION

This invention relates to a method to detect the presence or determine the concentration of microorganisms in a solution by regulating light reaching or emitted by a fluorophore encapsulated in a chemically inert light transparent matrix.

BACKGROUND OF THE INVENTION

Microorganisms present in bodily fluid can be detected using a culture bottle. Generally, a culture bottle is a flask allowing positive cultures to be detected rapidly. The flask is generally a transparent closed container filled with nutrient that promotes the growth of the organism. In particular, bacteria in blood can be detected in culture. U.S. Pat. No. 4,772,558 (Hammann).

Many different qualitative and quantitative detection means are used to monitor the growth of microorganisms in a culture bottle. The microorganisms in a culture bottle have been detected by use of external detectors such as a magnifying lens, U.S. Pat. No. 4,543,907 (Freudlich). Additionally, integral detectors such as liquid level indicators can show bacterial growth as a function of increased pressure in the vessel V. Swaine et al., EPA 124,193. Additionally, microorganisms can be detected by measuring changes in pH caused by bacterial growth, Mariel, G.B. Patent No. 1,601,689.

Still another method to detect microorganisms involves the use of a culture media that contains a compound which changes color or appearance according to the growth of microorganisms. The change in the media can be detected with a spectrophotometer. There are many examples of reactions used in Microbiology that rely on a color change. Bascomb, *Enzyme Tests in Bacterial Identification*, 19 Meth. Microbio. 105 (1987). For example. a variety of organisms can be classified in large part by their pattern of fermentation, oxidation or assimilation of carbon sources. Fermentation of carbohydrates results in the production of acid which causes a decrease in pH. This drop in pH can be easily detected by including a pH indicator like bromothymol blue or phenol red. With both indicators, acid conditions representing the fermentation of a particular carbohydrate result in a yellow color (changing from blue-green for bromothymol blue or pink/red for phenol red). The same approach can be adopted for a variety of carbohydrates, ranging from monosaccharides like glucose to polysaccharides like inulin. In an analogous fashion, increasing pH can also be monitored. Assays for detecting the presence of decarboxylase and urease, and the ability to use malonate are based on an increase in pH, as indicated by a color change in the indicator. Turner, et al. U.S. Pat. No. 4,945,060 discloses a device for detecting microorganisms. In this device changes in the indicator medium resulting from pH changes in CO$_2$ concentration in the medium are detected from outside the vessel.

Chemical and enzymatic reactions are used to detect or quantitate the presence of certain substances in microbiological or other assays. Many of these tests rely on the development or change of color or fluorescence to indicate the presence or quantity of the substance of interest.

Another approach to determine if an organism can degrade a particular substrate, is to use a reagent which is capable of reacting with one or more of the intermediates or final products. For example, the detection of the reduction of nitrate to nitrite. If nitrite is formed, then a pink to deep red color will result when sulfanilic acid and alpha-naphthylamine are added to the reaction mixture.

In contrast to the indirect detection of an enzymatic reaction illustrated by the nitrate/nitrite test, it is possible to use a synthetic analog of a natural substrate to directly indicate the presence of an enzyme. For example, methylene blue can be reduced under certain conditions by the action of reductase, resulting in a shift from blue to colorless. In another test, the oxidase assay relies on the interaction of cytochrome oxidase with N, N, N', N'-tetramethyl-p-phenylenediamine producing a blue color.

Another example is the ability of microorganisms to degrade sulfur-containing amino acids as indicated by the production of H$_2$S. Typically, the organism is incubated with a high concentration of a sulfur-containing substrate (e.g. cysteine, cystinc) in an acid environment. The production of H$_2$S is indicated by the formation of a black precipitate in the presence of ferric ammonium citrate.

Enzymes can usually act on more than one substrate. This allows for the use of synthetic enzyme substrates for the detection of enzyme activities. Synthetic substrates contain a metabolic moiety conjugated with a chromatic or fluorescent moiety. The conjugated molecule usually has a different absorption and/or emission spectrum from the unconjugated form. Moreover, the unconjugated chromatic or fluorescent moiety shows a considerably higher absorption or fluorescence coefficients than those of the conjugated molecule. This allows the measurement of small amounts of products of enzyme activities in the presence of the large amounts of conjugated substrate required for maximal enzyme activity. An example of a synthetic enzyme substrate is o-nitro-phenol-$\beta$-galactopyranoside used for the detection of activity of the enzyme $\beta$-galactosidase. The conjugated substrate is colorless. The $\beta$-galactosidase enzyme hydrolyzes the substrate to yield $\beta$-galactosidase and o-nitrophenol. o-nitro-phenol absorbs strongly at 405 nm, and its release can be measured by the increase in absorbance at that wavelength. Bascomb, *Enzyme Tests in Bacterial Identification*, Meth. Microbiol. 19, 105 (1987), reviewed the synthetic moieties used for enzyme substrates and the enzymatic activities measurable using this principle.

Presently, the monitoring of color or color end-product in chemical and microbial reactions is usually achieved in either of two ways; 1) the detection of color or color end-product can be achieved by visual observation and estimated qualitatively, or 2) the detection of color end-products or loss of color can be achieved by measuring the intensity of color instrumentally. Spectrophotometers that measure light absorbance are commonly used for this purpose. When measuring the concentration of a number of substances it is advantageous to use one instrument based on one principle of measurement, otherwise cost increased.

Although the use of colorimetric reactions is widespread there are limitations, especially in the sensitivity of detection. In order to improve sensitivity and, in the case of identification of microorganisms, thereby to decrease the time required to obtain a result, fluorescence-based methods frequently are used. Unfortunately, it may not be possible to develop a fluorescent equivalent to every assay. Additionally, the fluorescent reagents themselves may be highly toxic and therefore difficult to commercialize.

In such cases one might need to measure activities of some enzymes fluorometrically, the others colorimetrically. However, most instruments are suited to measure either absorbance or fluorescence, and very few can be used to measure both.

The general principle of fluorescence quenching has been accepted as a way to detect or determine enzymatic or chemical reactions. For example, Fleminger et al. synthesized intramolecularly quenched fluorogenic substrates for the assay of bacterial aminopeptidase, P. Fleminger et al., *Fluorogenic Substrates for Bacterial Aminopeptidase P and its Analogs Detected in Human Serum and Calf Lung*, Eur. J. Blochem. 125, 609 (1982). In this case, the fluorescence of the aminobenzoyl group is quenched by the presence of a nitrophenylalanyl group. When the enzyme is present, the nitrophenylalanyl group is cleaved, with a concommitant increase in the sample's fluorescence. A variety of enzymes have been assayed by this type of procedure, including hydrolytic enzymes, other amino- and carboxypeptidases and an endopeptidase. Yaron et al., *Intramolecularly Quenched Fluorogenic Substrates for Hydrolytic Enzymes*, Anal. Bioche. 95, 228 (1979); Carmel et al., *Intramolecularly—Quenched Fluorescent Peptides as Flurorogenic Substrates of Leucine Aminopeptidase and Inhibitors of Clostridial Aminopeptidase*, Eur. J. Biochem. 73, 617 (1977); Carmel et al., *An Intramolecularly Quenched Fluorescent Tripeptide as a Fluorgenic Substrate of Angiotensin-I-Converting Enzyme and of Bacterial Dipeptidyl Carboxypeptidase*, Eur. J. Biochem. 87, 265 (1978); Florentin et al., *A Highly Sensitive Fluorometric Assay for "Enkephalinase", a Neutral Metalloendopeptidase that Releases Tyrosine-Glycine-Glycine from Enkephalins*, Anal. Biochem 141, 62 (1984). In each of the previous approaches, a synthetic substrate containing a quenching group and a fluorescing group was generated in order to detect the activity of the enzyme.

An alternative to this approach would involve the synthesis of a resonance energy transfer pair of fluorescing groups on a substrate molecule. In this method, cleavage by the enzyme of one of the groups would result in a decrease in fluorescence, since the critical distance would be exceeded, eliminating the transfer of energy. However, the previously discussed approaches are limited to specifically designed substrates.

Still another approach involves the estimation of a chromophore by fluorescence measurement. See W. Blumberg et el., *Hemoglobin Determined in Whole Blood "Front Face" Fluorometry*, Clin. Hemo. 26, 409 (1980). Blumberg disclosed an assay based on attenuation of fluorescence of a dye, whose excitation wavelengths overlap with the absorption wavelengths of the chromophore.

Subsequently, M. Shaffar, U.S. Pat. No. 4.495,293 (hereinafter Shaffar) filed a patent application disclosing a method to fluorometrically determine a ligand in an assay solution using conventional fluorometric techniques. In Shaffer the intensity of the fluorescence emitted by the assay solution is related to the change in transmissive properties of the assay solution produced by the interaction of the ligand to be determined and a reagent system capable of producing change in the transmissive properties of the assay solution in the presence of the ligand. More particularly, Shaffar discloses a method to monitor absorbance using a fluorophore in solution with the chromophore. In this method the fluorophore may interact with the assay cocktail and produce changes in fluorescence intensity which are unrelated to the change being measured. The selection of the fluorophores is also restricted, in that pH dependent or environment sensitive fluorophores cannot be utilized. Additionally, when the fluorophore is in solution, less than accurate measure of absorbance may be obtained because light is absorbed exponentially through the chromophore sample.

Similarly, Beggs & Sand, EPA 91,837 disclosed a solution based method for determination of tryptophan-deaminase activity by measuring the reduction in fluorescence in the presence of a chromophore produced by the interaction between indole pyruvic acid and metal ions using a fluorophore "whose fluorescence is capable of being quenched by the indole pyruvate-metal ion complex, the ions of the fluorophore being present throughout the incubation period".

Also, Sands, U.S. Pat. No. 4,798,788 discloses a process to detect a nitrate reducing microorganism by measuring reduction of fluorescence in solution by causing the diazotization of the fluorophore. In all these cases a specific fluorophore needs to be chosen for each test to ensure that it will fluoresce under the conditions of the test, e.g. only few fluorophores fluoresce at pH of less than 2.0.

SUMMARY OF THE INVENTION

This invention provides a method to use a fluorophore encapsulated in a chemically inert matrix which is transparent at the wavelengths of interest. The fluorophore, positioned to intersect the transmission light path, indirectly monitors absorbance or changes in the absorbance of a chromophore encapsulated or isolated by a gas permeable polymetric matrix. The use of a fluorophore encapsulated in or isolated by a matrix allows for the sequential influence of reaction components on the intensity of light detected. This result can be achieved when the absorption spectrum of a chromophore overlaps the excitation and/or the emission spectrum of a fluorophore, thereby allowing the change in fluorescence to be related to the intensity of color in the reaction and consequently related to the quantity of the substance of interest. It should be noted that the spectrum is not limited to visible light.

More particularly, this invention relates to a multi-layer body fluid culture sensor comprised of a pH sensitive absorbance based dye spectrally coupled to a pH insensitive, or pH sensitive dye that is highly buffered, fluorescence based dye. The pH sensitive absorbance based dye is encapsulated or isolated by a polymeric layer that is permeable to $CO_2$ and water, but impermeable to protons. The pH insensitive fluorophore is encapsulated or isolated in the second polymeric layer that may or may not be permeable to $CO_2$ and water.

This type of sensor may be used to detect or determine the concentration of microorganisms in bodily fluid. The spectral criterion required to make this determination are such that the absorption spectrum of the chromophore must overlap the excitation and/or emission spectrum of the fluorophore, thereby allowing the change in fluorescence to be related to the change in the reaction and consequently related to the presence or quantity of the substance of interest.

Further, this sensor is used to monitor microbial infections grown in a fluid culture bottle. In particular, this sensor can be used to monitor bacterial growth. As bacteria grow they generate $CO_2$. The $CO_2$ generated by the bacteria diffuses into the polymeric layer that is in direct contact with a hydrated pH sensitive absorbance based dye. The $CO_2$ reacts with the aqueous environment to form carbonic acid ($H_2CO_3$), which lowers the pH of the absorbance dye environment. This results in a concomitant change in the pH sensitive spectrum of the dye. Typically, as the absorbance of an absorbance based dye decreases more light reaches the fluorophore for excitation which results in a larger amount of emitted fluorescence.

In one embodiment the gas permeable, proton impermeable polymeric matrix is silicone. Additionally, in one embodiment of this invention a detector, such as a photomultiplier tube, is placed under the blood culture bottle to detect fluorescent emission.

DETAILED DESCRIPTION - BEST MODE

Figure 1:
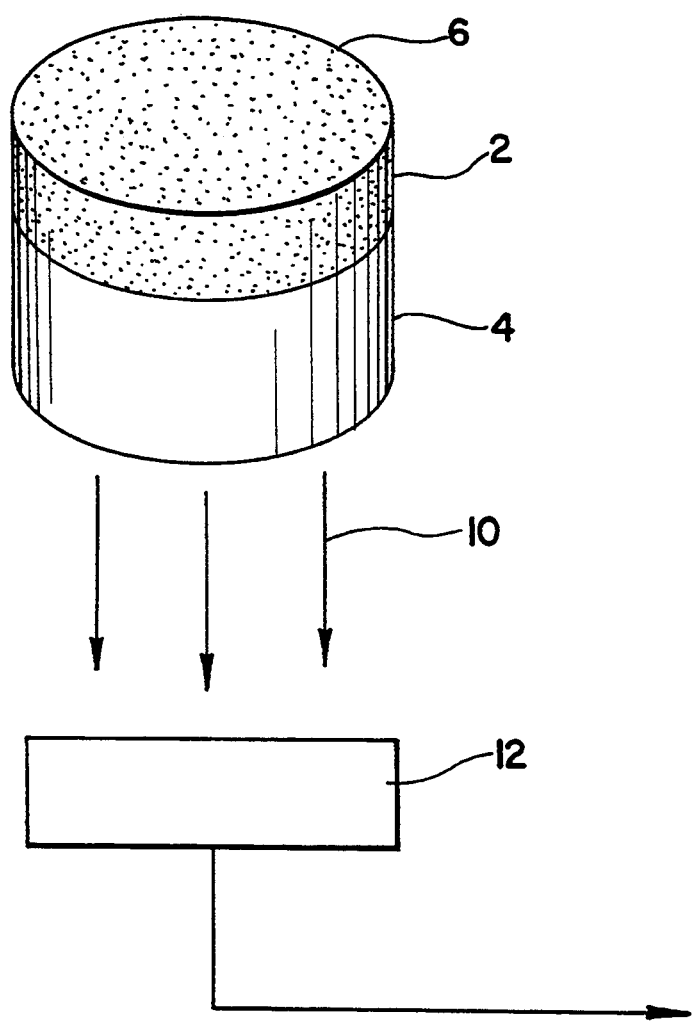
FIG. 1 shows a schematic diagram of a multi-layer blood culture sensor.

In this approach, fluorescence from a fluorophore embedded in a chemically inert light-transparent matrix, is modulated by a pH sensitive absorbance dye encapsulated in a polymeric gas permeable, but proton impermeable matrix. The assay is carried out in a blood culture bottle.

In a fluorometric based colorimetric assay the fluorescence intensity is regulated by changes in absorbance of an interfering chromophore. As a pH change occurs the chromophoric material alters the amount of light reaching the fluorophore and/or the amount of emitted light reaching the detector. Spectrally compatible colorimetric and fluorometric indicators are selected so that as the pH changes due to the production of $CO_2$ by microorganisms present in the sample, the colorimetric indicators regulate the amount of light reaching the fluorophore and/or photodetector and, thus cause a change in the amount of emitted light from the fluorescent dye received by the photodetector. This change is detected with a fluorescent reader and can be correlated with the presence or concentration of microorganism in the sample.

A bodily fluid culture sensor is comprised of a pH sensitive absorbance based dye encapsulated in or isolated by a polymeric gas permeable, but proton impermeable matrix and a fluorescent dye in a second polymeric matrix.

Spectrally compatible colorimetric and fluorometric indicators are selected so that when an organism is present in a sample, the colorimetric indicator will regulate the amount of light reaching the fluorophore thereby causing a change in the emission intensity from the fluorescence dye reaching the photodetector. The change, indicating the presence of bacteria, is detected with a fluorometric reader.

More particularly, spectrally compatible fluorescence and absorbance dyes are selected so that as carbonic acid ($H_2CO_3$) is produced, the absorbance of the dye will change thereby regulating the amount of light reaching the fluorophore and/or photodetector, thus producing a change in the measured fluorescence. This change is detected with a fluorescence reader. Spectrally compatible dyes are xylenol blue and rhodamine b. Additionally, bromothymol blue and rhodamine 101 are also spectrally compatible.

Thus, in practice a culture bottle containing the appropriate growth media can be inoculated with $E.\ coli$. As the organism grows, it produces $CO_2$ gas. The silicone is permeable to the $CO_2$. The $GO_2$ diffuses into the absorbance layer and reacts with water to produce carbonic acid ($H_2CO_3$). The carbonic acid causes a drop in the pH in the absorbance dye environment resulting in a change in measured absorbance. For example, as the pH drops in an absorbance layer containing the dye xylenol blue, the absorbance of xylenol blue decreases, thereby allowing more light to reach the fluorophore to excite it and thus increase the amount of fluorescence emitted at 590 nm. A positive culture using xylenol blue as the absorbance dye is detected by a measured increase in fluorescence as the xylenol blue decreases in absorbance.

The pH sensitive absorbance based dye is encapsulated in or isolated by a polymeric matrix that is gas permeable, but proton impermeable. The polymeric matrix must be optically transparent in the visible region, permeable to gas, autoclavable, stable for at least six months, and proton impermeable. In particular, silicone may function as the polymeric matrix used to encapsulate or isolate the absorbance based dye. Silicones found to meet these criteria were Dow, Rhone Poulenc, G. E. and Wacker.

Similarly, the fluorescence based dyes can also be encapsulated in a polymeric matrix. The polymeric matrix used for the fluorophore does not have to meet all of the above requirements listed for the matrix used to encapsulate or isolate the absorbance dye. The similar features that it must possess are that it must be optically transparent in the visible region, autoclavable and stable for at least six months.

The polymeric matrix containing or isolating the absorbance based dye must be coupled to the polymeric matrix containing the fluorescent dye. It should be noted that the polymeric matrices must be in close proximity so that light that has been regulated by the absorbance layer will have an effect on the emission intensity of the fluorophore as received by the photodetector. This can be accomplished by applying the same polymeric material to one side of each polymeric matrix and curing these matrices. Once the matrices containing the dyes have been adhered together they must be rehydrated. The clarity of the sensor upon rehydration is also a factor in matrix selection.

In the present invention, a bodily fluid culture sensor, FIG. 1, is comprised of a pH sensitive absorbance based dye encapsulated in or isolated by a polymeric gas permeable, but proton impermeable matrix 4 and a fluorescent dye in a second polymeric matrix 2. Reflective surface 6 can be included to facilitate the transmission of light to the detecting element 12. In FIG. 1 interrogation light enters the sensor and is regulated by pH sensitive matrix 4 which in turn causes a change in the fluorescence emission 10 of the fluorophore in matrix 2. This sensor offers the advantage of maximal surface area.

In an alternative embodiment, an acrylic encapsulated fluorophore or silicone embedded fluorescence material is adhered to an absorbance dye isolating polymeric layer, to make a two layer sensor.

In another embodiment, both the fluorescence and absorbance embedded material are poured into blood culture bottles. In this embodiment the fluorophore embedded silicone material is poured on top of absorbance embedded silicone.

The optical interrogation system comprises a visible output, 400–700 nm, light source focused onto one end of a bifurcated fiber optic cable. The common end is positioned close to the sensor, while the other end is positioned close to a photodetector, typically a photomultiplier tube. Appropriate excitation and emission filters are used to select wavelengths of choice for each dye. A beam splitter is used to divert a portion of the excitation light to a second photodetector and acts as a reference. A photodetector converts light to a current source which is converted to a voltage using an operational amplifier. A 12 bit analog to digital conversion offers sufficient dynamic range to read the voltage. A computer program is then used to read, plot and store data.

A measurement is taken by first reading reference light intensity. Next the reading from the sensor disk is measured. The data is plotted by taking the ratio of reference, excitation light, to sample. In particular, as $CO_2$ levels increase in the blood culture bottle, the absorbance of the absorbance dye changes, thereby changing the amount of light reaching the fluorescence layer and/or photodetector. This causes a change in emitted fluorescence that is detected.

The following examples serve to illustrate the method of the present invention. The concentration of reagents and other variable parameters are only shown to exemplify the methods of the present invention and are not to be considered limitations thereof.

EXAMPLE 1 XYLENOL BLUE—RHODAMINE 101 SENSOR

Wacker silicone elastomer 3601 part A is thoroughly mixed with Wacker 3601 catalyst part B in a 9:1 ratio, as recommended by the manufacturer. Next 5% w/w of a 50 mM xylenol blue, dissolved in 5 mM borate buffer pH 11 containing 1% Tween 80, is added to the silicone and homogenized to ensure a uniform distribution of the dye. The absorbance layer mixture is then poured into an aluminum square mold to a thickness of 30/1000 of an inch and cured at 55° C. for 2 hours.

Wacker silicone is prepared, as described above. Next 2% w/w of 7.5 mM Rhodamine 101, in 50 mM Tris-HCl buffer DH 8.5 in 95% ethylene glycol, is added to the silicone. The mixture is poured over the previously cured xylenol blue layer in the mold, described above, and cured at 55° C. overnight. This cured, dehydrated, double layer sensor consists of two distinct layers, each 30/1000 of an inch thick. Disks may now be punched out of the mold and adhered onto the base of bottles using more silicone, ensuring that the absorbance layer is face down. Finally, the bottles are cured at 55° C. for 15 minutes, rehydrated with normal saline and autoclaved on the wet cycle for 17 minutes. Saline is replaced with growth media and inoculated with *E. coli* by injecting a suspension with a sterile needle through the septum. The blood culture bottle is placed in the instrument and fluorescence emission is measured.

Figure 2:
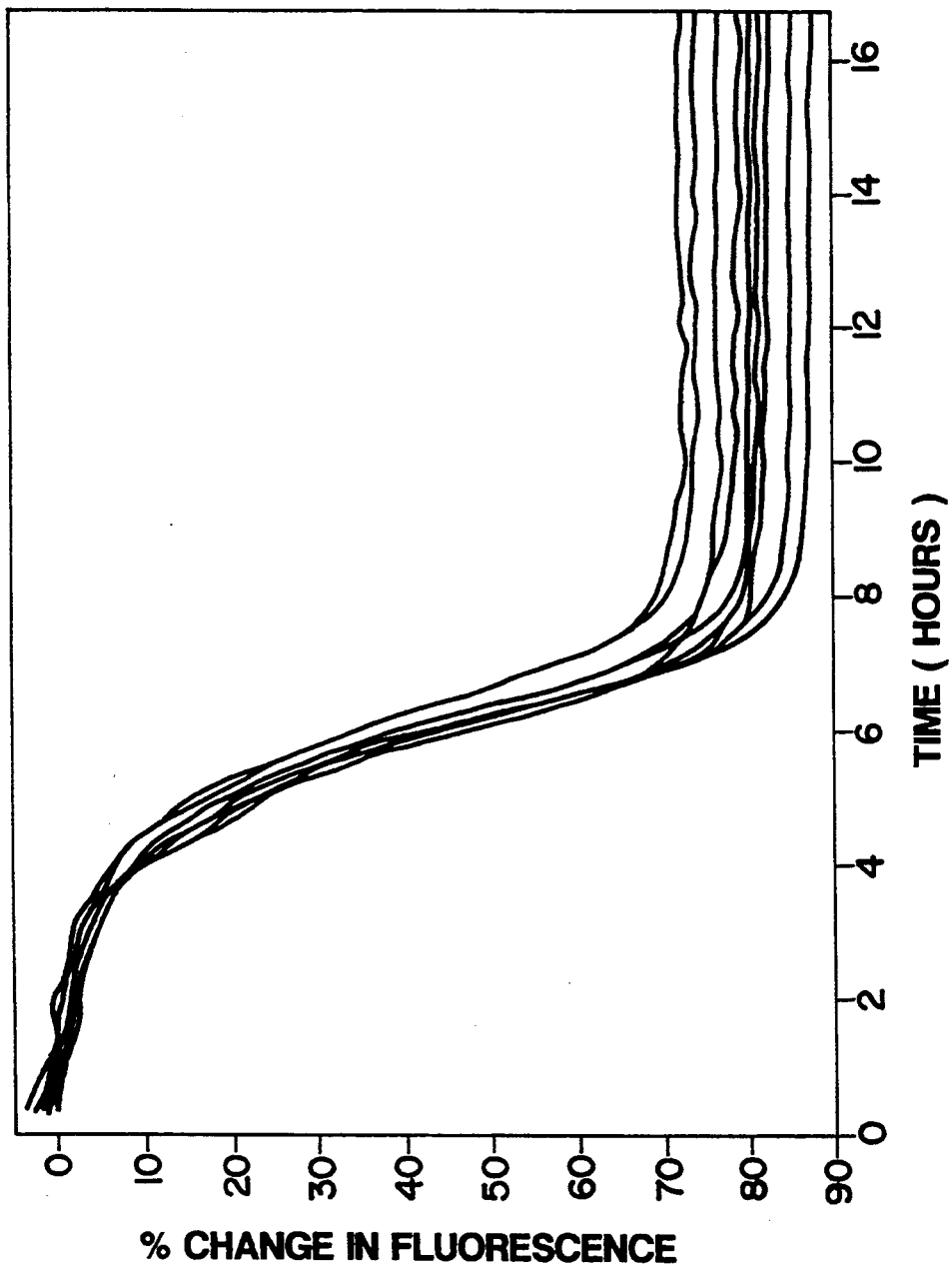
FIG. 2 shows a blood culture growth curve detected by a xylenol blue-rhodamine 101 sensor.

As the concentration of $CO_2$ increases in the blood culture bottle, the absorbance of the pH sensitive absorbance dye, xylenol blue, decreases, thus allowing more light to reach the fluorophore, rhodamine 101, to thus increase the amount of fluorescence emitted at 590 nM. This increase in fluorescence intensity v. time is shown in the blood culture growth curve at FIG. 2.

EXAMPLE 2 XYLENOL BLUE IN SILICONE/RHODAMINE B IN ACRYLIC

Rhone Poulenc silicone elastomer 141 part A is thoroughly mixed with Rhone Poulenc 141 catalyst part B in a 10:1 ratio, as recommended by the manufacturer. Next 1% w/w of a 100 mM xylenol blue solution pH 11, dissolved in 10 mM borate buffer containing 1% Tween 80, is added to the silicone and mixed thoroughly with a tongue blade to ensure uniform distribution of the dye. The absorbance layer mixture is then poured into an aluminum square mold to a thickness of 30/1000 of an inch. The mold is allowed to sit out on the countertop at room temperature for about one hour or until the bubbles have disappeared, at which time the mold is placed in the incubator to cure at 55° C. for two hours.

Rhone-Poulenc silicone is prepared, as described above. Next, a 40/1,000" thick acrylic disc (Glasflex, Inc.). approximately 1 cm in diameter, containing 0.2 grams/lb of rhodamine B (Sigma) is glued onto the above absorbance layer using the Rhone-Poulenc silicone at the 10/1 ratio as glue. The double layer sensor is then placed back in the 55° C. incubator for two hours to allow for adherence of the two layers. Following the curing, the double layer sensor is punched out with a cork borer, and glued onto the base of a Wheaton bottle, ensuring that the absorbance layer is face down, using the Rhone Poulenc silicone as mentioned above. The bottle is placed in the 55° C. incubator to cure for at least two hours. The bottle is then rehydrated overnite and tested the following day as described in Example 1.

Figure 3:
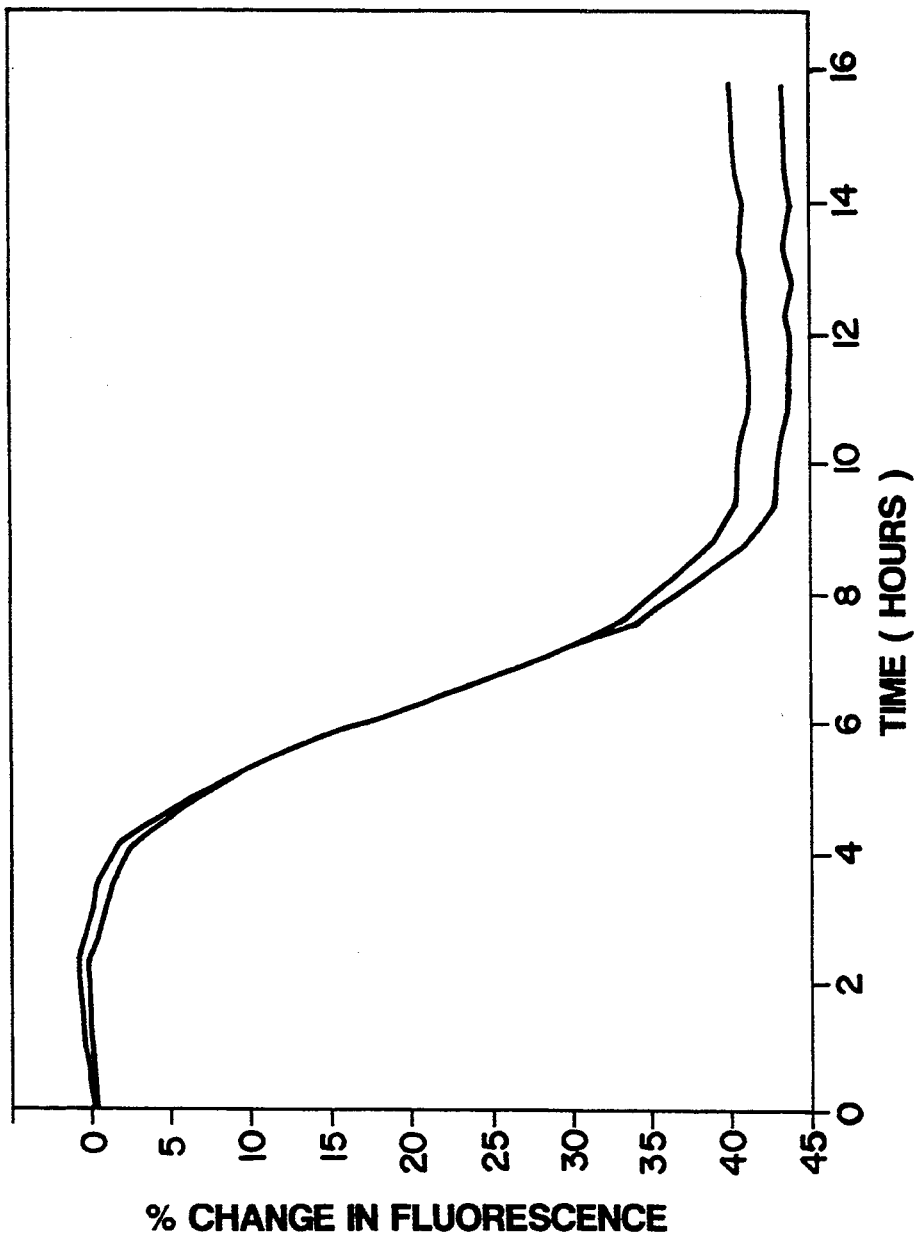
FIG. 3 shows a blood culture growth curve detected by xylenol blue in silicone-rhodamine B in acrylic sensor.

As the concentration of $CO_2$ increases in the blood culture bottle, the absorbance of the pH sensitive absorbance based dye xylenol blue decreases, thus allowing more light to reach the fluorophore (rhodamine B) doped acrylic, to thus increase the amount of fluorescence emitted at 590 nm. This increase in fluorescence intensity v. time is shown in the blood culture growth curve in FIG. 3.

EXAMPLE 3 XYLENOL BLUE IN SILICONE/6213 RED STANDARD ACRYLIC

Wacker silicone elastomer 3601 part A is thoroughly mixed with Wacker 3601 catalyst part B in a 9:1 ratio, as recommended by the manufacturer. Next 5% w/w of a 50 mM xylenol blue, dissolved in 5 mM borate buffer pH 11 containing 1% Tween 80, is added to the silicone and homogenized to ensure a uniform distribution of the dye. The absorbance layer mixture is then poured into an aluminum square mold to a thickness of 30/1000 of an inch and cured at 55° C. for two hours.

Next, a 40/1,000" thick acrylic disc (Gilasflex, approximately 1 cm in diameter, referred to as No. 6213 Red (Glassflex Standard Product) is glued onto the above absorbance layer using the Wacker silicone at the 9/1 ratio as glue. The double layer sensor is then placed back in the 55° C. incubator for two hours to allow for adherence of the two layers. Following the curing, the double layer sensor is punched out with a cork borer, and glued onto the base of a Wheaton bottle, ensuring that the absorbance layer is face down, using the Rhone Poulenc silicone as mentioned above. The bottle is placed in the 55° C. incubator to cure for at least two hours. The bottle is then rehydrated overnite and tested the following day as described in Example 1.

Figure 4:
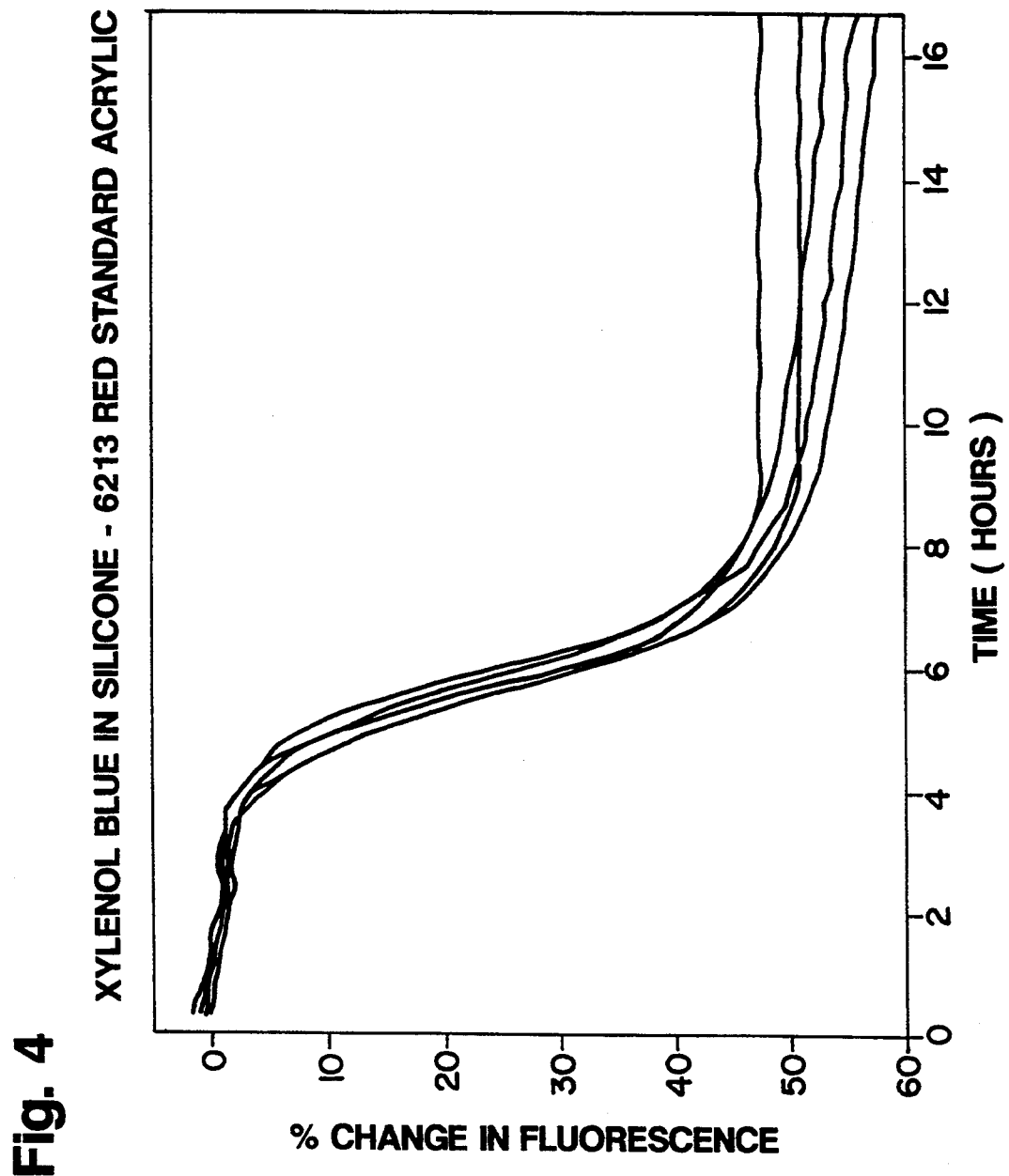
FIG. 4 shows a blood culture growth curve for a xylenol blue in silicone-6213 acrylic sensor.

As the concentration of $CO_2$ increases in the blood culture bottle, the absorbance of the pH sensitive absorbance based dye xylenol blue decreases, thus allowing more light to reach the fluorophore (rhodamine b) doped acrylic, to thus increase the amount of fluorescence emitted at 590 nm. This increase in fluorescence intensity v. time is shown in the blood culture growth curve in FIG. 4.

EXAMPLE 4 BROMOTHYMOL BLUE IN SILICONE/RHODAMINE 101 IN SILICONE

Wacker silicone elastomer 3601 part A is thoroughly mixed with Wacker 3601 catalyst part B in a 9:1 ratio, as recommended by the manufacturer. Next 5% w/w of 50 mM bromythymol blue, dissolved in 5 mM tris buffer pH 12 in ethylene glycol, is added to the silicone and homogenized to ensure a uniform distribution of the dye. The absorbance layer mixture is then poured into an aluminum square mold to a thickness of 30/1000 of an inch and cured at 55° C. for two hours.

Figure 5:
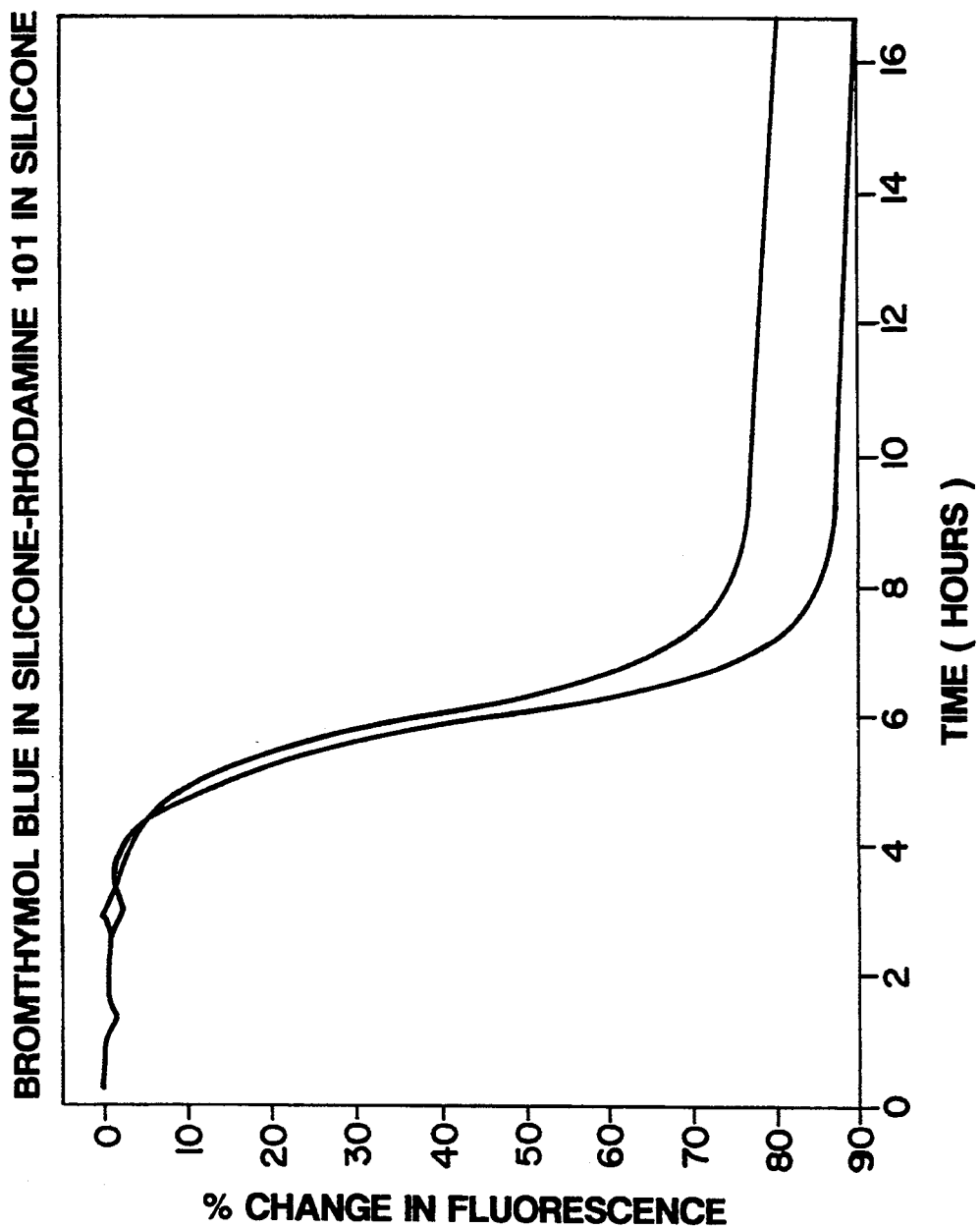
FIG. 5 shows a blood culture growth curve for a bromothymol blue in silicone-rhodamine 101 in silicone sensor.

Wacker silicone is prepared, as described above. Next 2% w/w of 7.5 mM Rhodamine 101, in 50 mM Tris-HCl buffer pH 8.5 in 95% ethylene glycol, is added to the silicone. The mixture is poured over the previously cured xylenol blue layer in the mold, described above to isolate the absorbance layer. This sensor is then cured at 55° C. overnight. This cured, dehydrated, double layer sensor consists of two distinct layers, each 30/1000 of an inch thick. Disks may now be punched out of the mold and adhered onto the base of bottles using more silicone, ensuring that the absorbance layer is face down. Finally, the bottles are cured at 55° C. for 15 minutes, rehydrated with normal saline and autoclaved on the wet cycle for 17 minutes. Saline is replaced with growth media and inoculated with *E. coli* by injecting a suspension with a sterile needle through the septum. The blood culture bottle is placed in the instrument and fluorescence emission is measured. The increase in fluorescence intensity v. time is shown in blood culture growth curve in FIG. 5.

Although this invention has been described with respect to specific embodiments, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A multi-layer sensor for determining the concentration or presence of a microorganism in a bodily fluid which comprises:
   a. a pH sensitive absorbance based dye encapsulated in a first light transmissive, gas permeable, proton impermeable matrix; and
   b. a pH insensitive fluorescence dye encapsulated in an inert light transparent second matrix, wherein said first and second matrices are spectrally coupled and in close proximity.

2. The multi-layer sensor of claim 1 wherein said pH sensitive absorbance based dye is selected from the group consisting of xylenol blue and bromothymol blue.

3. The multi-layer sensor of claim 1 wherein said fluorescence dye is selected from the group consisting of rhodamine 101 and rhodamine B.

4. The multi-layer sensor of claim 1 wherein said first and second matrices are selected from the group consisting of silicone and acrylic.

* * * * *